US006852069B2

(12) United States Patent
Park

(10) Patent No.: US 6,852,069 B2
(45) Date of Patent: Feb. 8, 2005

(54) METHOD AND SYSTEM FOR AUTOMATICALLY EVALUATING PHYSICAL HEALTH STATE USING A GAME

(75) Inventor: Seung-Hun Park, Kyoungki-Do (KR)

(73) Assignee: Codisoft, Inc., Suwon (KR)

( * ) Notice: Subject to any disclaimer, the term of this patent is extended or adjusted under 35 U.S.C. 154(b) by 0 days.

(21) Appl. No.: 10/480,190

(22) PCT Filed: Jun. 11, 2002

(86) PCT No.: PCT/KR02/01103

§ 371 (c)(1),
(2), (4) Date: Dec. 9, 2003

(87) PCT Pub. No.: WO02/101627

PCT Pub. Date: Dec. 19, 2002

(65) Prior Publication Data

US 2004/0171460 A1 Sep. 2, 2004

(30) Foreign Application Priority Data

Jun. 12, 2001 (KR) ................................. 10-2001-0032939
Mar. 30, 2002 (KR) ................................. 10-2002-0017621

(51) Int. Cl.⁷ ............................................... A63B 22/00
(52) U.S. Cl. ................................ 482/8; 482/9; 482/900
(58) Field of Search ......................... 482/1–9, 900–902

(56) References Cited

U.S. PATENT DOCUMENTS

| | | | | |
|---|---|---|---|---|
| 6,095,949 A | * | 8/2000 | Arai | 482/4 |
| 6,244,987 B1 | * | 6/2001 | Ohsuga et al. | 482/4 |
| 6,746,371 B1 | * | 6/2004 | Brown et al. | 482/8 |

* cited by examiner

*Primary Examiner*—Glenn E. Richman
(74) *Attorney, Agent, or Firm*—Notaro & Michalos PC

(57) ABSTRACT

A method and system for automatically evaluating the state of a user's physical health includes a game for maintaining the use's interest as he exercises and which automatically measures and evaluates the user's physical strength and health and provides an exercise prescription. The method has a game execution and measurement step performed via a main controller section with a display device, a memory and a virtual subject in the game space. Multiple standardized protocols are selected according to measurements reflected in the game and the virtual subject, reflecting an exercise state of the user on the basis of an exercise state of a reference person in the game. Measuring/reading/storing/displaying physical strength and health information occur after generating events for measuring the physical strength and health information such as particular situations, letters, sounds, voices, etc., in the game content.

9 Claims, 9 Drawing Sheets

METHOD AND SYSTEM FOR AUTOMATICALLY EVALUATING PHYSICAL HEALTH STATE USING A GAME

TECHNICAL FIELD

The present invention relates to a method of, and a system for, automatically evaluating physical health state using a game, and more particularly to a method of, and a system for, automatically evaluating physical health state using a game, which can automatically measure his physical strength and health information and evaluate his physical strength and health with automatic exercise prescription, while a user is exercising continuously and interestedly through a game without feeling boredom.

BACKGROUND ART

Generally, the present exercise prescription is carried out on the basis of basic inquiries based on questionaires, cardiac and pulmonary endurance power, agility, momentary power, muscular endurance power, evaluation of physical strength by evaluation of muscular power, heart rate by an electrocardiogram and its change, analysis of body fat, blood pressure, evaluation of physical strength by maximum oxygen intake($VO_2max$), etc., performed by each individual measurement apparatus, and thus it has disadvantages that systematic exercise administration cannot be performed and those processes are boresome.

In particular, although an apparatus for measuring physical strength and health information during exercise is developed, still it does not escape from boredom.

DISCLOSURE OF INVENTION

Accordingly, the present invention is made in order to solve the above problems, and one object of the present invention is to provide a method of, and a system for, automatically evaluating physical health state using a game, which can automatically measure his physical strength and health information and evaluate his physical strength and health with automatic exercise prescription, while a user is exercising continuously and interestedly through a game without feeling boredom.

Further, it is another object of the present invention to provide a method and system for automatically evaluating physical health state using a game, wherein, in one single apparatus, various factors to enable judgement of user's physical strength and health state can be automatically measured and evaluated, and exercise prescription can also be automatically performed.

It is still another object of the present invention to provide a method and system for automatically evaluating physical health state using a game, wherein, while a user is exercising through a game, user's physical strength and health information is automatically measured and transmitted, and user's physical strength and health can be evaluated using a network with automatic exercise prescription, and furthermore, using a network, exercise can be taken through a game under competition among multiple persons, and thus interest and promotion of health can be achieved.

To accomplish such objects of this invention, a method of automatically evaluating physical health state using a game is provided in accordance with one embodiment of the invention, in which, while a user is exercising using an exercise equipment, his physical strength and health information is obtained through diverse physical strength and health information sensing section, and then physical strength and health evaluation information and/or exercise prescription information can be obtained, said method being characterized by comprising: a game execution and measurement step of executing a game through a main controller section, a display device, a memory means, etc., as a virtual subject in the game space, multiple protocols standardized according to measurement requirements to be reflected in the game and said virtual subject reflecting an exercise state of the user on the basis of an exercise state of a reference person in the game, and the step of measuring/reading/storing/displaying physical strength and health information naturally after generating events for measuring the physical strength and health information such as particular situations, letters, sounds, voices, etc., in game contents.

Furthermore, a system for automatically evaluating physical health state using a game is provided in accordance with another embodiment of the invention, in which, while a user is exercising using an exercise equipment, his physical strength and health information is obtained through diverse physical strength and health information sensing section, and then physical strength and health evaluation information and/or exercise prescription information can be obtained, said system being characterized by comprising: a main controller section for controlling the physical strength and health information sensing section, a display device, a memory means, etc., so as to execute a game and measurement step for measuring/reading/storing/displaying physical strength and health information from the physical strength and health information sensing section naturally after generating events for measuring the physical strength and health information such as particular situations, letters, sounds, voices, etc., in the game contents, while executing a game templated as a virtual subject in the game reflecting an exercise state of the user on the basis of an exercise state of a reference person in the game so as to enable execution of the game through the display device by exercising by means of the exercise equipment and measurement of the physical strength and health information, and so as to measure/read/store/display the physical strength and health information in connection with the game execution; and a load adjustment section controlled by the main controller section so as to adjust load of the exercise equipment according to at least proceeding states of the game.

Still furthermore, the present invention enables automatized physical strength and health evaluation and exercise prescription by enabling to measure every physiological variable concisely in the state of unconsciousness with adding a game factor to be a game execution by exercise, and can realize a system which a basic question, physical strength and health evaluation, exercise prescription, and an exercise for promotion of health can be performed in a single system, respectively or all together, thereby achieving effective health administration. The embodiment of the present invention is also applied to an exercise equipment of a bike type, which does not limit the scope of the present invention. The bike has one advantage that it can remove an emergency situation occurring in a running machine and the protocol can be applied and can be evaluated with low load and by the same analogy in measuring every physiological variable for evaluating the physical strength and health as compared with the conventional measurement protocols.

BEST MODE FOR CARRYING OUT THE INVENTION

Now, a preferred embodiment of the present invention will be described in detail with reference to the accompanying drawings.

In this specifications, physical strength and health information means a term including all kinds of physical physiological health information, health information according to physical strength(physical strength information), all kinds of health information related to a user's body such as heart rate, respiration volume, blood pressure, weight, oxygen volume saturated in blood, momentum or exercise speed(running speed, etc.,) according to a user's exercise state, agility, momentary power, muscular power, softness, equilibrium, muscular endurance power, cardiac and pulmonary endurance power, NIBP, $VO_2$, change in heart rate, cooperation ability of body organs, etc. Physical strength and health evaluation information to be discriminated from the above term means a result obtained about a user's health degree by analyzing the physical strength and health information. For example, in a user whose weight is heavier as compared with his age, the user's age and weight belong to the physical strength and health information and fatness, while if it is judged on the basis of these, belongs to the physical strength and health evaluation information.

Figure 2:
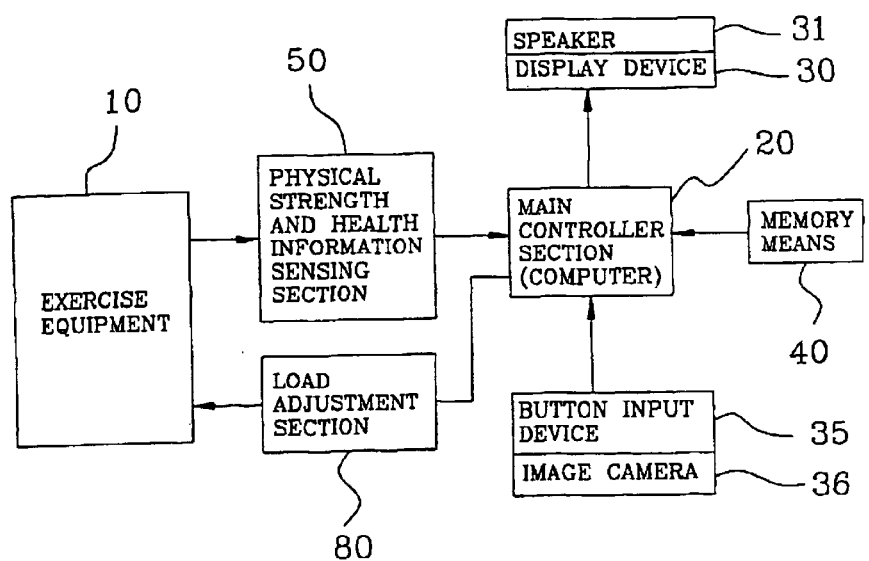
FIG. 2 is a block diagram showing a system for automatically evaluating physical health state using a game, with removing exercise equipment parts in FIG. 1.

First, FIG. 2 shows, as a block diagram, basic construction of a automatic physical strength evaluation and exercise system 100.

The automatic physical strength evaluation and exercise system 100 in FIG. 2 comprises an exercise equipment 10, a main controller section 20, a display device 30, a memory means 40, a physical strength and health information sensing section 50 and a load adjustment section 80.

Figure 1:
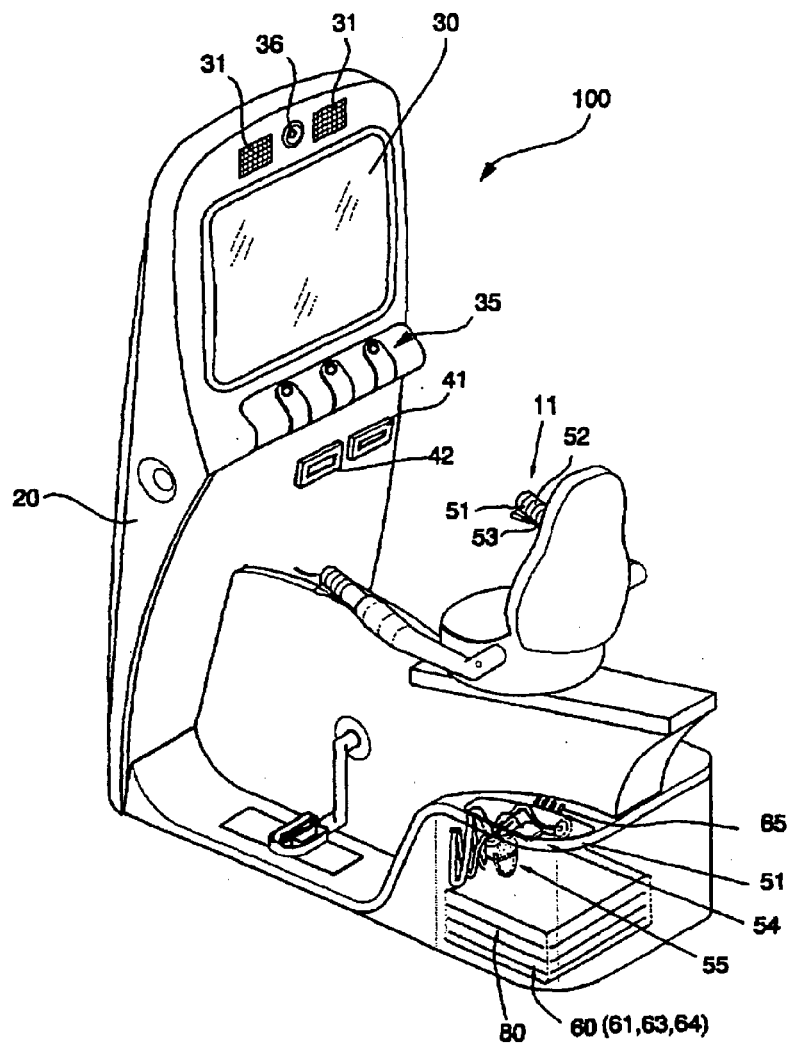
FIG. 1 illustrates main construction of a system with the appearance for performing a method of automatically evaluating physical health state using a game in accordance with the present invention.

The exercise equipment 10 may include, but is not limited to, a health bike shown as an example in FIG. 1. Physical strength and health information according to user's exercise is sensed in the physical strength and health information sensing section 50. The sensed and read physical strength and health information is transmitted to the main controller section 20, which analyzes the physical strength and health information, generates physical strength and health evaluation information about user's health state, and diagnoses the user's health state. The generated physical strength and health evaluation information is displayed in the display device 30.

Figure 7:
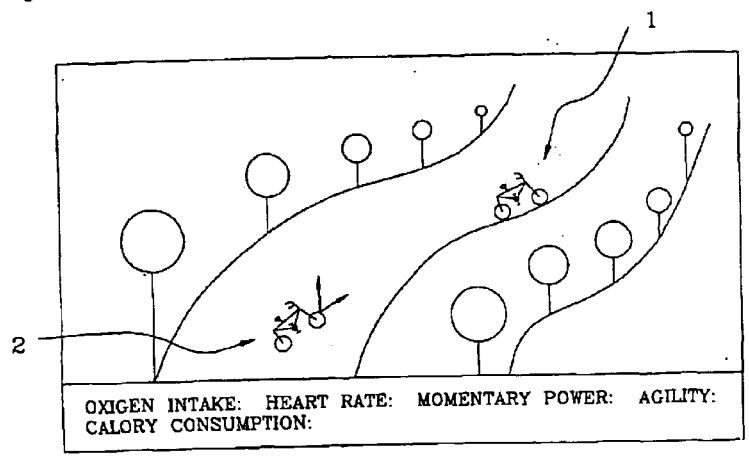
FIG. 7 shows a sample screen for construction of a game for embodying the present invention.

Furthermore, the user executes a predetermined game stored in the memory means 40 while being exercising, in order not to feel bordom. Referring to FIG. 7, a reference person 1 and a virtual subject 2 to reflect user's momentum appear in the game, the virtual subject 2 or the reference person 1 being able to have any figure which can induce user's interest according to the conventional art, such as diverse characters, interesting animal figures, etc. Also, the user can take pictures of his own diverse figures using an image camera 36 in order to make his own appearance displayed as the virtual subject 2 to reflect the user's momentum(exercise speed). Further, it is possible to compose a predetermined background scene and his exercising appearance using a chroma-key method. a user can exercise with other users by means of a network 95 such as an internet, etc., instead the exercising together with the reference person 1, which system will be explained in detail in connection with FIG. 9.

Figure 3:
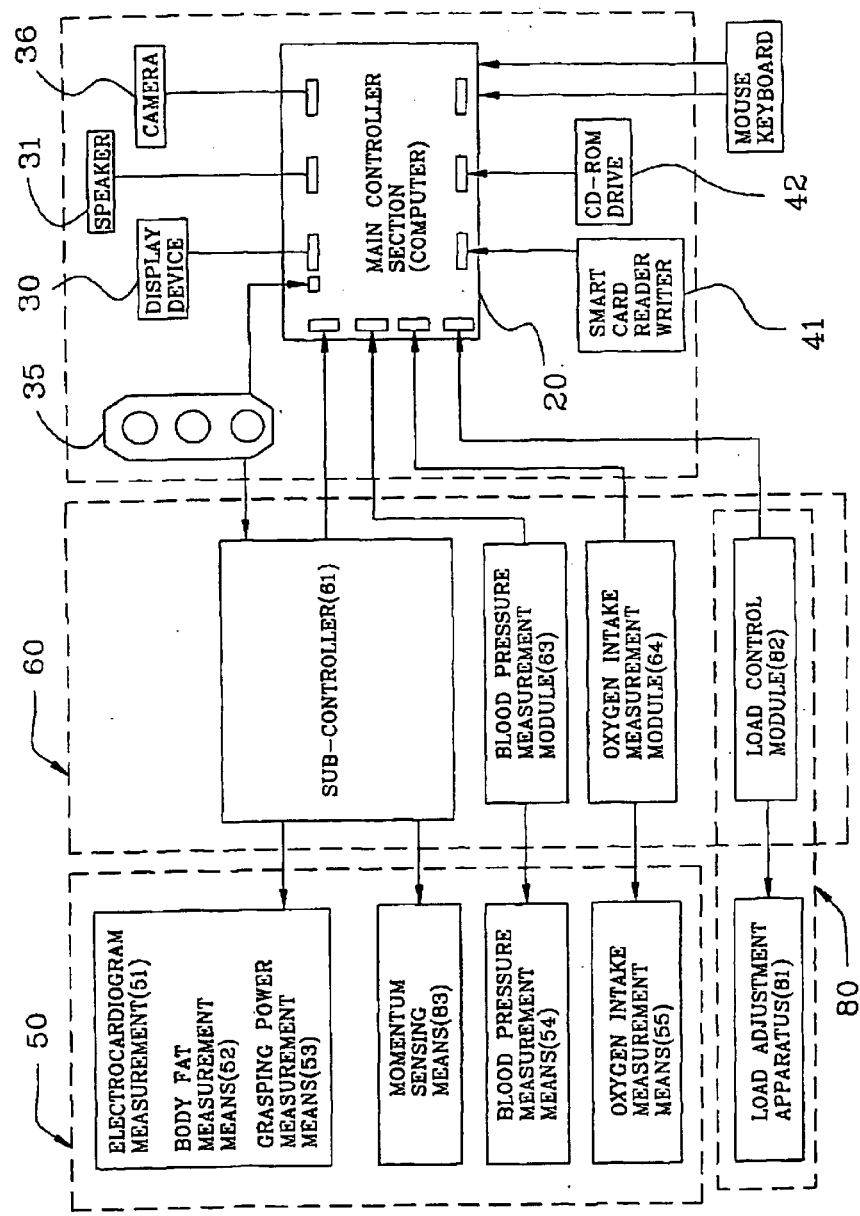
FIG. 3 illustrates construction, in accordance with one embodiment of FIG. 2.

A button input device 35 is provided so that the user may select a desired menu among diverse menus for diverse health measurement. As information to be able to be inputted through the button input device 35, there will be a diagnosis by questions about a health state, etc. The button input device 35 may comprise a selection button in the middle and a cancel button and a movement button in the left and right sides, as shown in FIG. 1. Also, a Keyboard and/or a mouse can be included as shown in FIG. 3, in order to input information such as a member ID, a password, a name, a resident registration number, sex, age, weight, height, etc. The main controller section 20 may comprise diverse menus to enable a diagnosis of the user's health state, and the physical strength and health information read in the physical strength and health information sensing section 50 according to the menus. The following example is explained so as to facilitate understanding of the invention.

The physical strength and health information sensing section 50 may comprise diverse measurement modules, an example of which is shown in FIGS. 1 and 3. The physical strength and health information sensing section 50 is installed in the exercise equipment 10, and thus it is advantageous that information about the user's self exercise state can be measured simultaneously with the user's exercising and without measuring health or exercise information separately.

For example, the weight scales may be provided in a saddle or a footboard of the exercise equipment 10. Then, user's weight can be measured by getting up or sitting on the exercise equipment 10, such measured user's weight being transmitted to the main controller section 20. Further, a body fat measurement means 52 for measuring the user's fatness, as shown in detail in FIG. 10, may be installed in a handle 11 of the exercise equipment 10. By installing the body fat measurement means 52 in the handle 11, user's fatness can advantageously be measured the during the exercise without any necessity to measure it separately.

The main controller section 20 provides the physical strength and health evaluation information aftering executing diagnosis about the user's health state on the basis of the transmitted physical strength and health information. For example, whether to be fat or not can be analyzed by only two pieces of physical strength and health information regarding body fat and weight. The more diverse the physical strength and health information to be read in the physical strength and health information sensing section 50 is, the more diverse is the physical strength and health information to be able to diagnose in the main controller section 20. For example, the main controller section 20 can calculate the rotation number of a bike wheel or a pedal and the exercise distance while the user exercises for around 12 minutes, and a Broker index(weight/(height−100)=100: 90–100: normal; 101–119: fat; 120 or the above: severe fat) can be calculated using the user's weight and height inputted through the button input device 35. Further, the body fat can be calculated using the bioelectric resistance analysis method, and the heart rate by an electrocardiogram and its change, agility about how fast the user responds to the given situation, etc., can be measured.

In FIG. 1, main construction of a system with the appearance for performing a method of automatically evaluating physical health state using a game in accordance with the present invention is illustrated, and in FIG. 3, one example construction in accordance with one embodiment of FIG. 2 is illustrated.

In FIGS. 1 and 3, a system for physical strength evaluation, exercise prescription, and health promotion comprises mainly three parts of the main controller section 20 like a computer system, the exercise equipment 10 and several measurement means 51, 52, 53, 54 and 55 of the physical strength and health information sensing section 50 with the load adjustment section 80, and the controller 60.

The computer system comprises a memory means 40 of every program and data such as a hard disk, a ZIP drive, a CD ROM drive 42, etc., and may comprise a backup means and/or a database server, and also the display device 30 such as a TFT LCD module, an image camera 36, a speaker 31, a smart card reader/writer 41, and a microphone(omitted in the drawings) as connected peripheral devices.

Various measurement means 51, 52, 53, 54 and 55 of the exercise equipment 10 comprise a electrocardiogram measurement means 51 as one biosignal measurement sensor for health diagnosis, a body fat measurement means 52 located at the handle part for analyzing body fat, a grasping power measurement means 53 of a handle type similar to a bike brake for evaluating muscular power, a blood pressure measurement means 54, an oxygen intake measurement means 55 of a flow sensor for detecting maximum oxygen intake etc., and the button input device 35 is utilized to evaluate agility. The load adjustment section 80 for adjusting drive load of the exercise equipment 10 comprises a load adjustment apparatus 81 and a load control module 82(shown in FIG. 3). In FIG. 1, the main controller section 20, the controller 60 and the load adjustment section 80 are dispersedly installed in the apparatus part of the exercise equipment 10, but the controller 60 and a load control module 82 of the load adjustment section 80 can also be installed in the inside of the main controller section 20 in an interface card form of an ISA or a PCI type.

The main controller section 20 or a computer system, separately stored various measurement means(see FIG. 1: 51, 54 and 55) of the exercise equipment, and the controller are communicated with four serial ports 65 using cables. Each communication is also constructed so as to communicate with a sub-controller 61 or a controller of the three buttons for confirming agility and proceeding questions, a blood pressure measurement module 63, the smart card reader/writer 41, and the load control module 82 for controlling drive load of the bike Each construction of every measurement means 51, 52, 53, 54 and 55 are described hereinafter.

Figure 10:
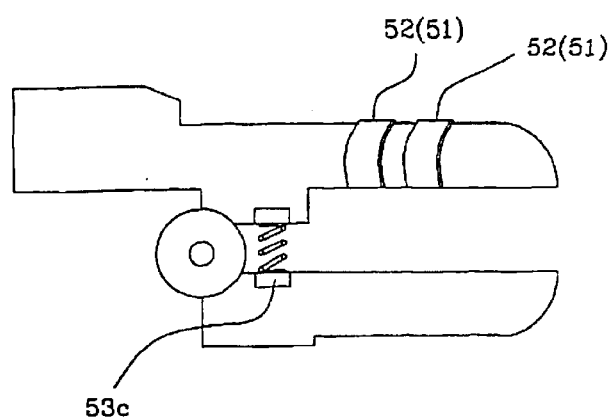
FIG. 10 shows schematical construction as one example of a grasping power measurement means and a body fat measurement means for embodying the present invention.

The grasping power measurement means 53, as shown in FIG. 10, can comprise a load cell as a structure similar to a brake of the bike, and preferrably, is constructed so as to prevent dispersion of the power to be capable of being caused when a left side and a right side are separate and measurement occurs concurrently, thereby achieving exact measurement. Through such grasping power measurement, the evaluation of a muscular power can be achieved.

In the electrocardiogram measurement means 51 of a high class, three leads are used and monitored from the beginning to the end of the measurement, presenting heart rate at stabilized time, maximum heart rate and heart rate at recovering time and being utilized for evaluating cardiac and pulmonary capability. In case of a low class, after-described body fat measurement means 52 can be used for combined use.

The body fat measurement means 52, as shown in FIG. 10, is installed at the handle 11 at which the grasping power measurement means 53 is located, and is performed by measuring a bio-impedance using total four contact points consisting of two contact points at opposite hands, thereby evaluating fatness degree.

The oxygen intake measurement means 55 comprises a spirometer of an oxigen mask shape, measuring maximum oxigen intake and using for evaluating cardiac and pulmonary endurance power.

Figure 11:
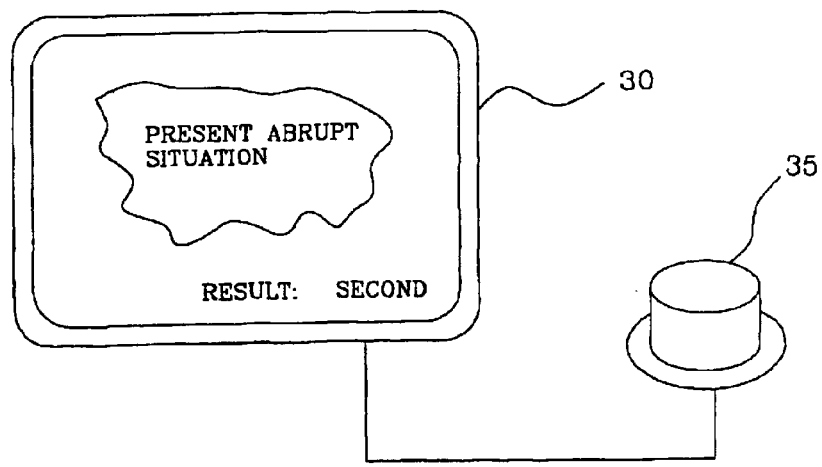
FIG. 11 is a block diagram showing one sample construction for measuring agility in accordance with the present invention.

Meanwhile, the button input device 35 is utilized for examining agility. The examination of agility can be achieved, differently from the general methods, by pressing the button responsive to an event given by presenting abrupt situation on a screen, as shown in FIG. 11, while displaying a game and evaluating physical strength, that is, by being established so that management on the situation is performed. In this case, agility is evaluated by a time difference between an outbreak of the event and the pressing action of the button. Preferably, such situations are presented several times on the game space for evaluating the physical power, and at each time the pressing speed of the user(a response speed against the presented situation) are repeatedly measured, from which error factors(for example, considering maximum/minimum range or constant range) are removed and an average value is obtained.

Furthermore, the load of the exercise equipment 10 is adjusted according to the kind, the level and the proceeding state of the game. The present invention is constructed so that the user may follow a preceding reference person 1 in a templated game, and the load adjustment section 80 comprises a load adjustment apparatus 81 and its load control module 82 so as to adjust load of the pedal according to each different situation(adjustment of inclination, ground surface state, etc.,) given by stages of the protocol to be displayed on a screen. Further, the load adjustment apparatus 81 may consist of a common brake device, or may be constructed diversely such as changing of gears, or inclination of the exercise equipment 10.

Meanwhile, by comprising a smart card reader/writer 41, the present invention can be constructed so as to store user's personal information and the present information of physical strength and health state through his recent measurement result and achieve a continuous administration of the user's information and exercise. First, the personal information is stored through the smart card reader/writer 41, the result just before the present measurement at every measurement is shown, and the change in the physical strength and every physiological variable is written in other memory means 40(other backup device, a hard disk, a ZIP drive, a CD ROM, a database) and administered, thereby enabling to construct the present invention so that an administration of a systematic momentum and an exercise method may be performed.

Furthermore, the image camera 36 may be used for purposes comprising a method showing a screen briefly after storing user's appearance before executing measurement, a method using the stored appearance as information constructing the virtual subject 2 reflecting the user in the game environment, an image chatting in the virtual space connected with a network such as LAN, etc., a service on the network to use a series of image cameras with an internet phone, etc. A speaker can be used at the same time with an image camera, a microphone, etc., for various guidances assisting measurement of the user or an internet phone, an image voice chatting, etc., through the network such as LAN, etc. The microphone can be used for an answer to the questions, etc., voice orders for various actions, an image voice chatting, etc.

Figure 4:
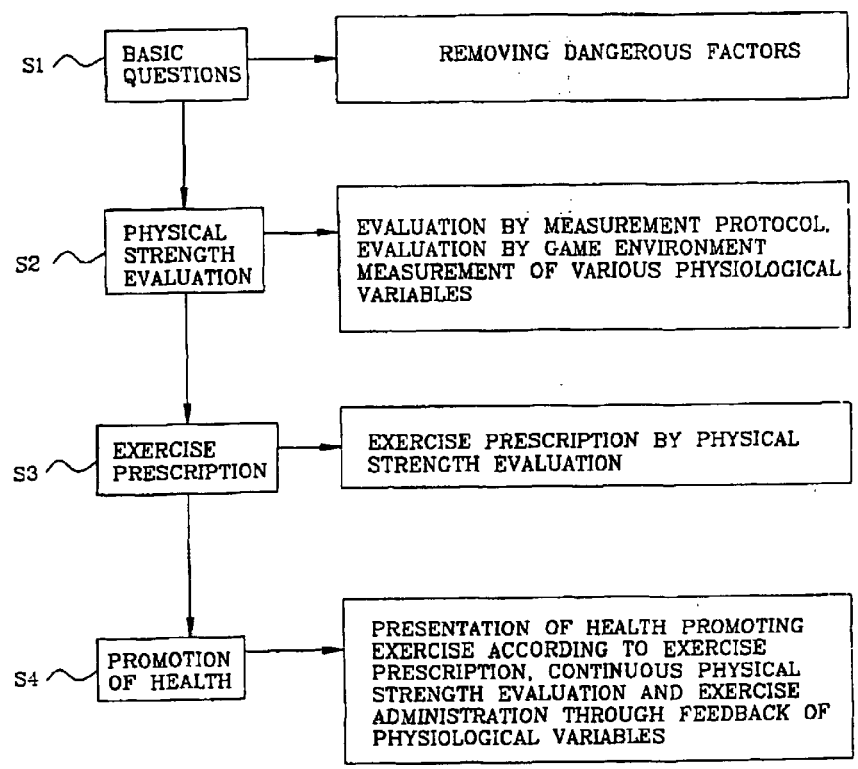
FIG. 4 is a flow chart illustrating the whole construction in accordance with one embodiment of a method of the present invention.
Figure 5:
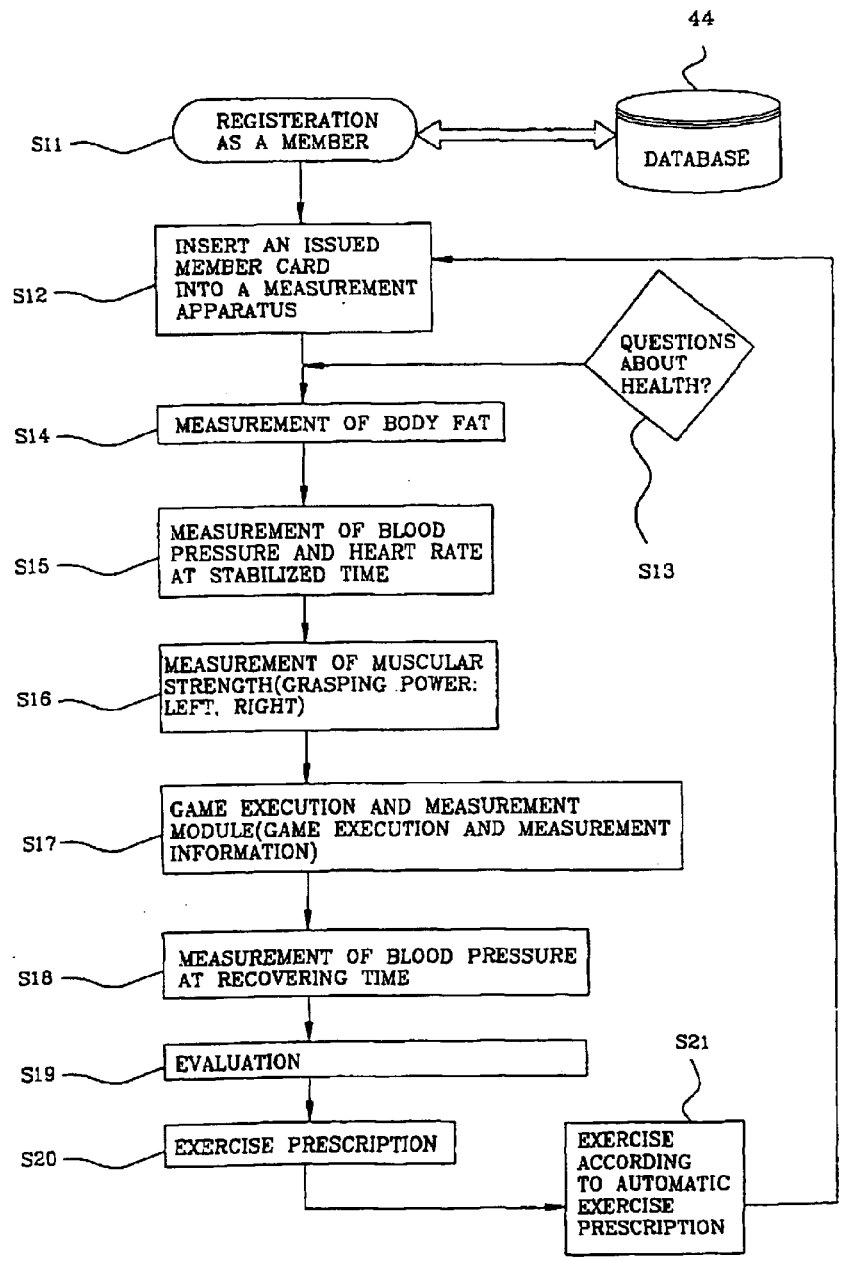
FIG. 5 is a concrete flow chart for a physical strength evaluation module in FIG. 4.

In FIG. 4, the whole construction in accordance with one embodiment of a method of the present invention is illustrated as a flow chart, and in FIG. 5, a concrete flow chart for a physical strength evaluation module in FIG. 4 is illustrated. Also, in FIG. 6, a concrete flow chart for a game execution and measurement module in FIG. 5 is illustrated as an example.

In FIG. 4, a method of automatically evaluating physical strength with exercise using the automatic physical strength evaluation and exercise system 100 of the present invention, may mainly comprise the steps of asking basic questions, evaluating physical strength according to measuring protocol, prescribing exercise using the physical strength evaluation, and exercising for promoting health with achieving bio-feedback of various physiological variables after the exercise prescription, in steps S1 to S4.

In step S11 of FIG. 5, the user or the measured person registers as a member and receives a member card. On issuing the member card, various body information such as height, weight, age, girth, etc., is stored in a database 44.

The question of health may comprise steps 1 and 2. The step 1 classifies a healthy person, a diabetic, a hypertensive, a cardiac disorder patient, a muscle and skeleton disorder patient, etc., through basic questions, which are used as materials for removing dangerous factors to be able to occur on the physical strength evaluation and for judging the health state. The step 2 provides with different questions by healthy or various disorder patients, and then detailed classification about the stage of health is performed. That is, by using a classification(man, woman, the old and the weak) obtained from the physical information of a patient inputted in the beginning and a classification item(healthy patient and various disorder patients) divided by the basic questions, physical strength evaluation protocol proper for each individual can be provided, or certain or all measurement of physical strength evaluation can be prohibited for various disorder patients, thereby being able to remove dangerous factors(various factors of danger in life or physical functions) to be able to occur on the physical strength evaluation. Also, there is an effect to be able to induce hospital treatment because a diagnosis of disease can be made by means of relationship among various physiological variables obtained by such information and physical strength evaluation.

The question of health can be made by a method of writing directly on various questionaires or a method of performing various input(by operation of the button input device 35 or a mouse, confirmation by voice, other various kinds of inputting methods) of the user or the patient as to the questions, which are displayed in order or totally on the display device 30(a TFT LCD, a CRT Monitor, etc.) in the present system, or explained by voice.

In the physical strength(physical strength related to health and exercise) evaluation of step S2 in FIG. 4, various questions are made for evaluating basic physical strength evaluation displayed on the screen in step 13 in FIG. 5, and, then various physiological variables will be measured as the following order. That is, measurement of body fat for 10–15 seconds, measurement of blood pressure(at stabilized time), measurement of heart rate(at stabilized time) and measurement of left and right muscular strength, as physical strength and health information which should be measured besides the above questions or is convenient to measure before application of measurement protocol for a game execution and measurement step of step 17 are made in step S14 to S16 in FIG. 5.

Figure 6:
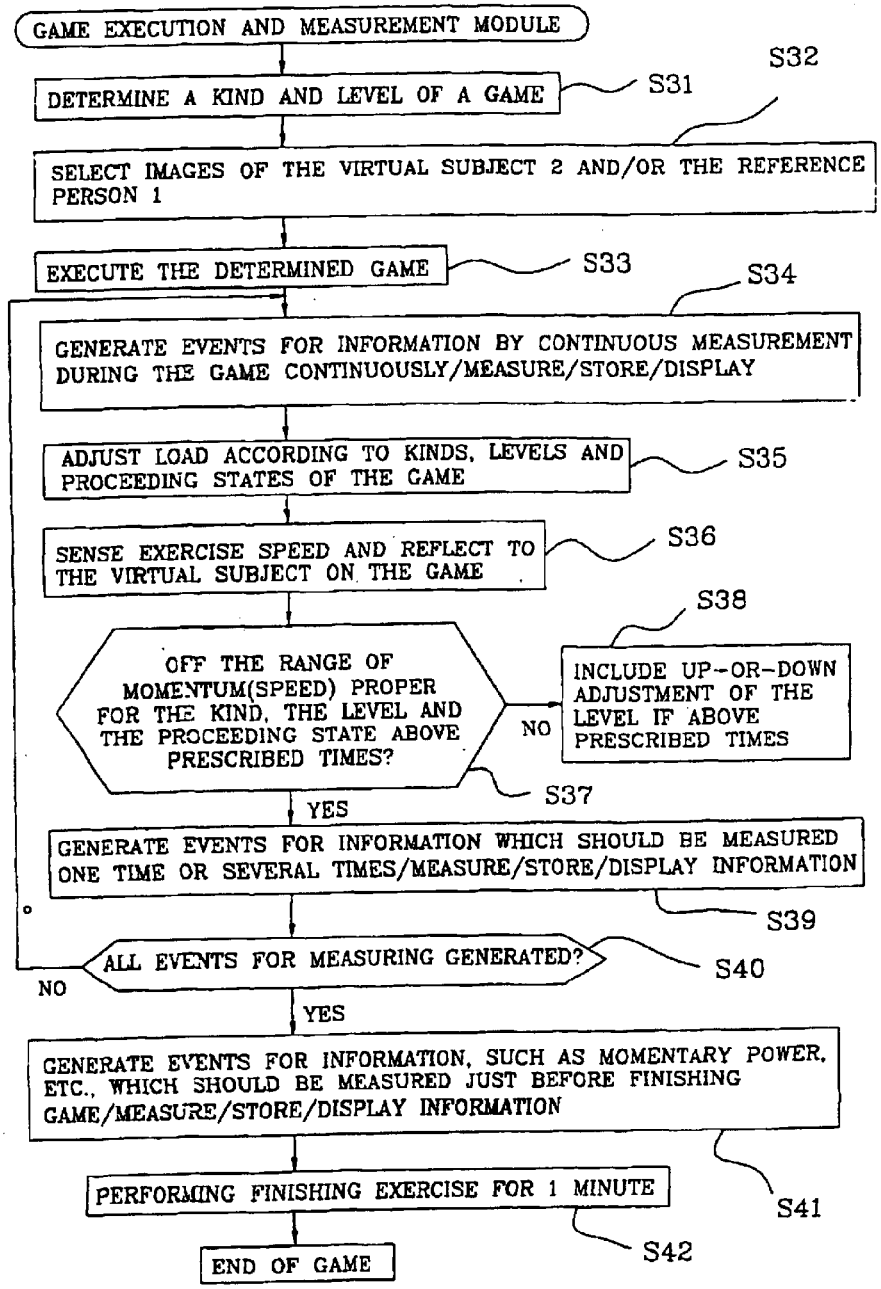
FIG. 6 is a concrete flow chart for a game execution and measurement module in FIG. 5.

In step S17 of FIG. 5, the game execution and measurement step according to the present invention is executed, for instance, for 8 minutes, wherein measurement of the physical strength and health information such as heart rate, oxygen intake, agility, momentary power, muscular endurance power, and cardiac and pulmonary endurance power is made, which should be measured during performing a game reflecting multiple protocols standardized according to measurement requirements. In such protocols of measurement, when a kind and a level of a game is determined in step S31 and images of the virtual subject 2 and/or the reference person 1 are selected in step S32, the determined game is executed in step S33, as shown in FIG. 6 for example. In step S34, the corresponding events for physical strength and health information which should be measured continuously during the game are generated continuously, and then the measuring results are stored and displayed. In the event that the measurement is impossible, up-or-down adjustment in a level of the game can be induced.

In step S35, load of the exercise equipment 10 is adjusted by means of the load control module 82 and the load adjustment apparatus 81 of the load adjustment section 80 according to kinds, levels and proceeding states of the game. In step S36, the exercise speed of the measured person or the user is measured by means of a momentum sensing means 83 such as rpm sensor, etc., and reflected by the virtual subject 2 in the game. In common, the user's momentum can be known from added load and sensed exercise speed. Such momentum sensing means 83 can be included by the load adjustment section 80 and a momentum signal such as the exercise speed, etc., to be sensed can be supplied to the main controller section 20 through the load control module 82. Otherwise, the momentum sensing means 83 can be included by the physical strength and health information sensing section 50 and the momentum signal can also be supplied through the sub-controller 61.

Even in this event, when the user's exercise goes off the range of momentum(speed) proper for the kind, the level and the proceeding state of the game in step S37 above prescribed times since the speed is too fast or slow, it is preferable to induce so as to up-or-down adjust the level of the game.

Then, in step S39, events for physical strength and health information which should be measured one time or several times during the game are generated one time or several times, and then the physical strength and health information is measured, which is stored in the memory means 40 and displayed in: the display device 30. Even in this event, when the measurement is impossible, it is preferable to induce so as to up-or-down adjust the level of the game.

When the events for every measurement are finished by repeating such event generation(step S40), events for physical strength and health information, such as momentary power, etc., which should be measured after finishing the game execution are generated in step S41 and the physical strength and health information is stored and/or displayed after being measured. Then the game is finished after performing finishing exercise, for example, for 1 minute in step S42. In step S18 of FIG. 5, after finishing application of the measurement protocol as above, measurement of blood pressure at recovering time is made, and in step S19, evaluation of physical strength according to measurement protocols as above, is performed. In step S20, exercise prescription(corresponding to step S3 in FIG. 4) through the physical strength evaluation is performed, and exercise for promoting health according to automatic exercise prescription can be executed. At this time, as explained in connection with step S4 of FIG. 4, it is preferable that bio-feed back of various physiological variables after the exercise prescription.

As described in the above, the basic physical strength and health evaluation comprises one part achieved using the game to effectively show various protocols obtained by preceding input of physical information and answers to the questions of health, and other part achieved by taking a series of action in the present system according to output means provided in the present system or the output means and various voice guidance. Information about cardiac and pulmonary endurance power(heart rate), agility(pressing of buttons) and momentary power(can be obtained by performing maximum exercise for a short period, for instance, the momentary power=$W=0.065=N/T$, where load is equal to $W=0.065$, W is weight, N is the number of rotation, and T is a time taken in performing one rotation of a pedal) can be obtained through the former. Through the latter, information about muscular strength(grasping power), fatness degree (body fat) and cardiac and pulmonary endurance power(can be obtained from blood pressure and heart rate or $F=N$, where F is average load applied to the exercise equipment 10, and N is the number of rotation of the exercise equipment 10) can be obtained. That is, in the order of physical strength and health evaluation, measurement of body fat, blood pressure at stabilized time, heart rate and muscular power are performed, and then while the user is performing a game containing effectively various protocols to be applied to the measured person or the user for a prescribed time(for instance, 8 minutes), information about heart rate, oxygen intake, agility, momentary power, muscular endurance power, cardiac and pulmonary endurance power can be obtained using the game.

The game may be constructed with various configuration (various stages reflecting various environments, degree of difficulty, etc.) which various protocols can be applied to. The virtual subject 2 to be indicated reflecting the measured person and the reference person 1 to proceed are appeared inside of two or three dimensional space representing in the output means. The present invention is embodied to the bike for removing various measurement danger factors. Change in heart rate on measurement is measured by a method in which three electrodes are attached to the body with simplified three lead type of electrocardiograph or by a method in which hands are in contact with electrodes located at the handle part to measure the grasping power and the body fat.

If physical strength and health evaluation begins, certain measurement which a game is not reflected to is performed, and then, the measured person executes a game which certain protocols for the user are reflected to by the above-mentioned method. If the game begins, the measured person perceives the reference person 1 to proceed at a certain speed and the virtual subject 2 to reflect a state of himself in the output means concurrently, and proceeds the game by rotating the pedal of the system in order to follow the virtual subject inside of the game. During the game proceeding, the speed of the reference person 1 can be given to be constant, but, diverse load environment is provided for the measured person by adjusting load of the pedal according to various game environments(various environmental changes to be able to expect an increase of load such as a rising hill, a sand road, etc.,) representing various protocols. Further, each speed of the measured person to be changed continuously during measurement and each load at certain points can be used in calculation of work made during the whole measurement and calculation of other various measurement. That is, the measured person rotates the pedal fast or slow according to the game, thereby increasing or decreasing the speed of the virtual subject 2 to reflect himself in the game by reflecting the pedal ratation speed. The agility is evaluated by calculating response time using a time difference between an outbreak of the event and an input of the measured person where the particular event is presented and the measured person takes one of various input types for solving this event when the game is executed for prescribed time. It is preferable to repeat such similar events and to obtain an average value In FIG. 8, construction for explaining the process of exercise prescription in FIG. 4 is shown.

Through the basic questions, the degree of the physical strength and health evaluation can be determined. In the case it is difficult to evaluate the physical strength and health because the measured person suffer from sever disease, the danger factors can be prevented beforehand. In the physical strength and health evaluation, men, women and the old and the weak are classified, and different protocol is applied, in which gradual increase and decrease of load per the total time is applied differently. When the physical strength and health evaluation is finished, measured physiological variables are analyzed synthetically, and a synthetical physical strength and ability index, an exercise-related physical strength index, a health-related physical strength index, etc., are presented with being classified into 15 stages. Also, health age related to these is presented and analysis opinion is made. By doing as above, it is possible to analyze automatically by means of objectified materials through an application of analysis template for the physical strength and health evaluation.

Figure 8:
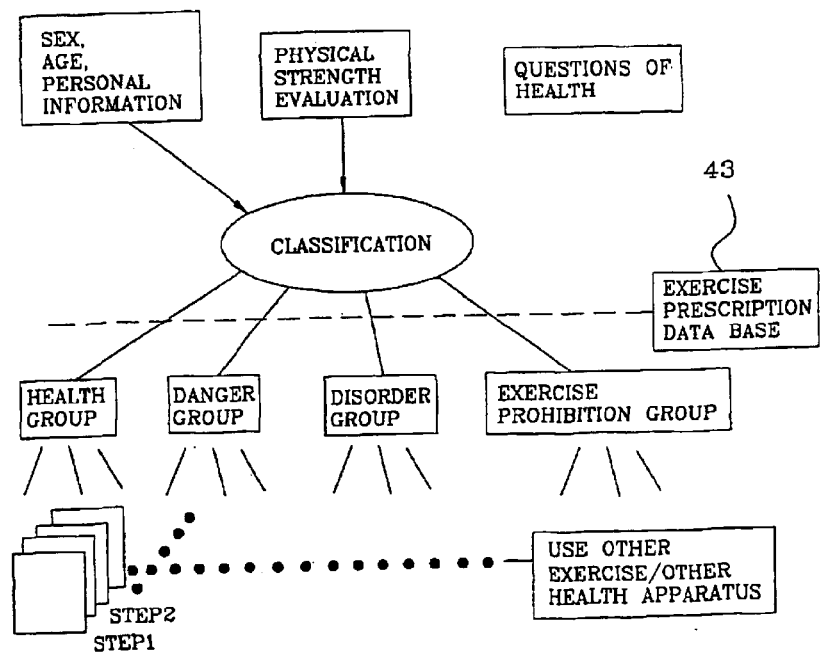
FIG. 8 illustrates construction for explaining a process of exercise prescription in FIG. 4.

In the exercise prescription, by analyzing the measured physiological variables synthetically after the physical strength and health evaluation is performed, a synthetical physical strength and ability index, an exercise-related physical strength index, and a health-related physical strength index are presented with being classified into multiple stages. Also, health age related to these and analysis opinion are presented on the output means or in a output form. As shown in FIG. 8, the exercise prescription is performed according to the following flow after evaluating the physical information of the measured person, question examination materials and the various physiological variables obtained through the game synthetically, and is calssified into, for instance, a health group, a danger group, a disease group and an exercise-prohibition group.

In this event, the exercise prescription proper according to each classified group is made. Presented exercise prescription is general exercise(walking, jogging, running, swimming, etc.), exercise using general health apparatus(a running machine, a health bike, various muscle power advance apparatus, etc.), and/or games using the system in accordance with the present invention. The game may be a series of template type game predetermined according to the various exercise prescription for the measured person, said game being in a single game type or a complex game type. The game to be applied according to the exercise prescription is discriminated in the present system and provided, or taken in the form of reflecting sports or game elements which the user prefers. The game may be executed according to the fixed exercise prescription or may be provided in the form of being able to remove dangerous factors capable of occurring during exercising by reflecting change of the various physiological variables(heart rate and its chage, maximum oxygen intake, etc.) fed back continuously through the game.

Health promotion exercise can be arranged using the system of the present invention according to each exercise prescription related to fatness, strengthening of cardiac and pulmonary capability, strengthening of muscle and articulation function, and promotion of growth with basic exercise (walking, running, bicycle, etc.). Such health promotion exercise step can also be performed by raising the level of the reference person 1 in the game, and moreover by presenting a competitor in the game using a network.

Figure 9:
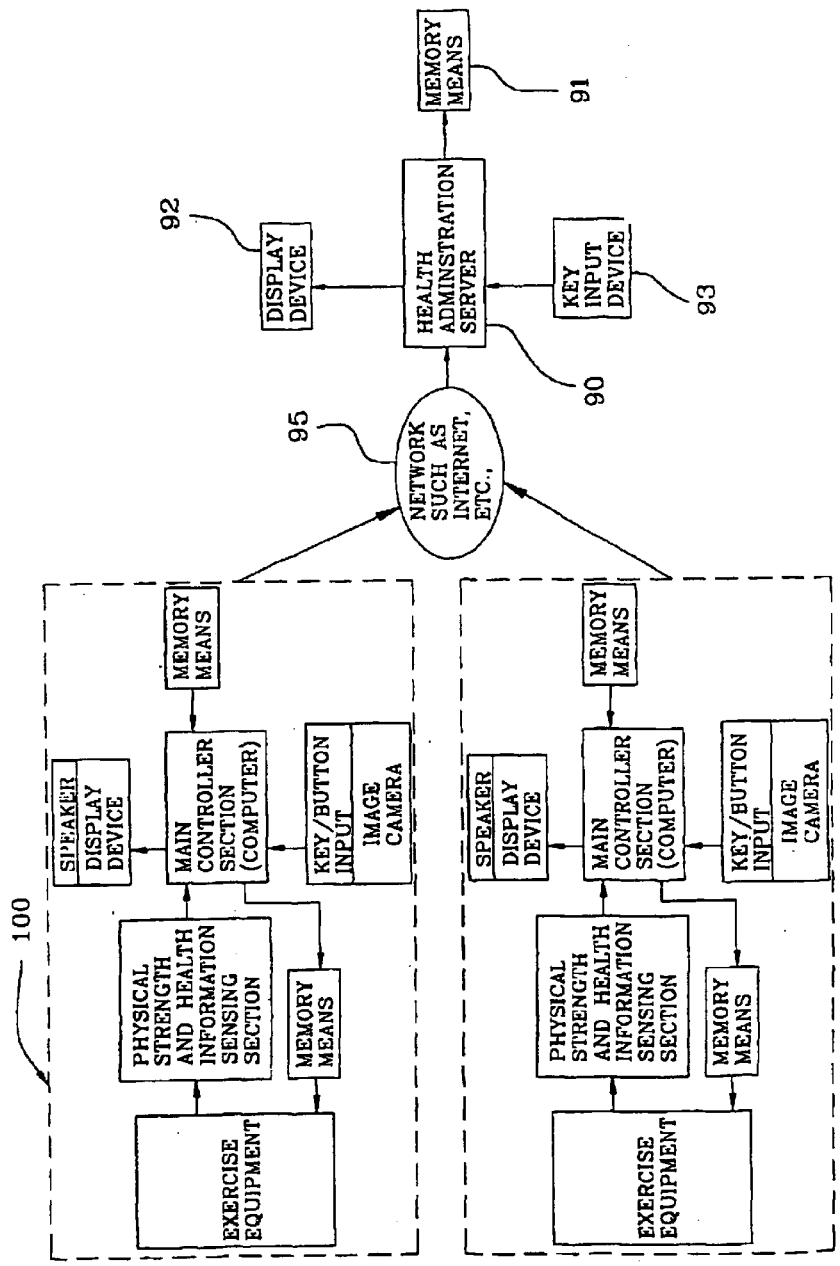
FIG. 9 is a block diagram of construction for embodying one method in accordance with the present invention using a network.

In FIG. 9, construction for embodying one method in accordance with the present invention using a network is illustrated as a block diagram.

With such construction of the network, a health adminstration server 90 can also provide each individual health adminstration service, and in this event, each client comprises the automatic physical strength evaluation and exercise system 100 and a connecting means. The health adminstration server 90 is preferably constructed so as to build up and utilize a database for each member by means of a separate memory means 91. A database management server may also be comprised. By such constructions, it is possible to transmit the physical strength and health information from the automatic physical strength evaluation and exercise system 100 to the health adminstration server 90, and receive the physical strength and health evaluation information and the exercise prescription information from the health adminstration server 90 in the automatic physical strength evaluation and exercise system 100. In addition, each data, update programs, etc., can be provided. Provision of a display device 92 and a key input device 93 for the automatic physical strength evaluation and exercise system 100 facilitates diverse remote health administration by an administrator and/or a specialist. Further, in the abovementioned game execution and measurement step, the classification of the user's health state is analyzed and, if an abnormal state or a change in the abnormal state is generated, the abnormal state or the change in the abnormal state is informed to a physician in charge by means of wired or wireless communication, and thus the physician in charge can take necessary measures through wired or wireless communication after analyzing the user's health/physical strength state precisely. It is also possible that the user's physical strength and health information and/or physical strength and health evaluation information is reported to the physician in charge or an exercise(nutrition) prescription specialist through a network 95 such as an internet, etc., and to the health adminstration server 90 so as to be delivered to, and analyzed by, the physician in charge or an exercise (nutrition) prescription specialist. Also, information on the present physical state and ID, recent exercise prescription and a state of recently practiced exercise can be stored in a smart card in the form of an XML(eXtensible Markup Language) data format, etc. The most recent information can also be stored by means of synchronization of the automatic physical strength evaluation and exercise system 100 and a database server of the XML or a relation type connected to the health adminstration server 90 directly or via a internet.

Also, by connecting two or more competitioners and presenting them as multiple competition subjects of the game on each display, they can share the virtual space of the game, and promote each health through interest and competition. Even in this event, preferably the health adminstration server 90 is constructed so that clients may be selected as competitioners by level or by classification. For this, each momentum or exercise speed of each client(even between the clients executing the different games) is reflected in the competition subjects of the game by being transmitted to each other, and thus competition with each other can be made.

According to the configuration and acting of the method of, and the system for, automatically evaluating physical health state using a game in accordance with the embodiments of the present invention described above, the user's physical strength and health information can be automatically measured during his exercising, and his physical strength and health with exercise prescription can be automatically analyzed and evaluated, while the user is exercising continuously and interestedly through a game without feeling boredom. Also, various physical strength and health information, etc., to enable judgement of user's physical strength and health state can be automatically measured and evaluated with exercise prescription in one single apparatus. Furthermore, while the user is exercising through the game, the user's physical strength and health information can be automatically measured and transmitted using the network, and the user's physical strength and health can be evaluated with exercise prescription using the network, and using the network, exercise can be taken through a game under competition among multiple persons, and thus interest and promotion of health can be achieved.

What is claimed is:

1. A method of automatically evaluating physical health of a user while the user is exercising using exercise equipment (10) having a sensor section (50) for sensing physical strength and a plurality of kinds of health information of the user, a main controller section (20) for executing a game with a game space for the user to perform and including a virtual subject (2) simulating the user and a reference person (1) in the game space, the controller section also capable of generating physical strength and health evaluation information based on the physical strength and plurality of kinds of health information sensed by the sensor section, the equipment also including a display device (30) for displaying information to the user and a memory means (40) for storing sensed information, evaluation information and the game, the method comprising:

executing the game through the main controller section, display device and memory means for generating events of the game to test the users physical strength and health;

measuring and storing the physical strength and plurality of kinds of health information of the user resulting from the events using the sensor section;

causing the virtual subject to reflect an exercise state of the user based on the sensed physical strength and kinds of health information, and on a plurality of protocols for the game based on an exercise state of the reference person; and generating and storing evaluation information based on the sensed physical strength and kinds of health information using the controller section and memory means.

2. A method according to claim 1, wherein said executing and measuring steps comprise at least one of measuring, reading, storing and displaying the physical strength and health information at least once per event or continuously during the game while generating the events continuously;

adjusting loads presented to the user of the exercise equipment by means of a load adjustment section (80) according to kinds, levels and proceeding states of the game; and up-or-down adjusting a level of the game and restating the game when the measuring is outside a selected range that is indicative of the user going outside a range of motion that is proper for measurement of the physical strength and health information according to a kind of game, a level of the game and a state of the game.

3. A method according to claim 1, including providing a remote health administration service by connecting to a health administration server (90) through a network (95), transmitting the physical strength and health information to the health administration server, and receiving the physical strength and health evaluation information, and exercise prescription information corresponding to the physical strength and health evaluation information from the health administration server.

4. A method according to claim 1, including reporting to a physician in charge, an abnormal state or a change in an abnormal state of the evaluation information based on the sensed physical strength and kinds of health information of the user, by means of wired or wireless communication, the physician in charge taking corrective measures through wired or wireless communication after analyzing the user's stats.

5. A method according to claim 1, including reporting at least one of the user's physical strength and health information and health evaluation information to a physician in charge or an exercise prescription specialist through a network (95) and a health administration server (90) so as to be analyzed by the physician in charge or the exercise prescription specialist.

6. A method according to claim 1, including, before said game executing and measuring step, at least one of the steps of:

selecting at least one of a game kind and level considering the user's sex, age, infirmity, or physical state;

selecting an image for at least one of the virtual subject (2) and the reference person (1) among images inputted through a camera (36) or stored picture images; and measuring at least some physical strength and health information before said game executing step; and after said game executing end measuring steps, at least one of the steps of:

measuring, reading, storing and displaying physical strength and health information, such as momentary power, which should be measured after the game, with generating the corresponding events after the game;

evaluating the user's physical strength and health by providing physical strength and heath evaluation information on the basis of an analysis map of a database constructed by software after finishing measuring the physical strength and health information and analyzing the physical strength and health information synthetically, said physical strength end health evaluation information being classified into multiple stages of at least one of a synthetical physical strength and ability index, an exercise-related physical strength index, and a health-related physical strength index;

prescribing an exercise by selecting and presenting exercise prescription information corresponding to the physical strength and health evaluation information from a database (43), said database (43) being classified by level on the basis of items of the physical strength and health evaluation information and constructed by different games with different degrees of difficulty; and before said exercise prescribing step, at least one of the steps of:

answering basic questions for the user; and reading personal physical strength and health information from a smart card or the memory means (40) or storing personal physical strength and health information at the smart card or memory means (40).

7. A system for automatically evaluating physical health state of a user while the user is exercising, comprising:

exercise equipment (10) for use in testing a user's physical strength and health information;

a sensor section (50) for sensing physical strength and health information of the user using the exercise equipment, from which physical strength and health evaluation information or exercise prescription information is be obtained;

a main controller section (20) for controlling the physical strength and health information sensor section (50);

a display device (30):

memory means (40) for storing a game to be executed with the exercise equipment, the physical strength and health information and the physical strength and health evaluation information or exercise prescription information, for execution of the game and for measurement steps for at least one of: measuring, reading, storing, and displaying the physical strength and health information from the physical strength and health information sensor section (50) after events are generated for measuring the physical strength and health information;

the main controller section presenting content to the user while executing the game as a virtual subject (2) in the game, reflecting an exercise state of the user on the basis of an exercise stats of a reference person (1) in the game and so as to enable execution of the game through the display device (30) by exercising by means of the exercise equipment (10) and measurement of the physical strength and health information; and a load adjustment section (80) controlled by the main controller section (20) so as to adjust load of the exercise equipment (10) according to at least proceeding states of the game.

8. A system according to claim 7, wherein said physical strength and health information sensor section (50) comprising:

at least one of: a button input device (35) for judging agility; an electrocardiogram measurement means (51); a body fat measurement means (52); a grasping power measurement means (53); a blood pressure measurement means (54); a oxygen intake measurement means (55); and a momentum sensing means (83); and a controller (60) comprising at least one of a sub-controller (61), a blood pressure measurement module (63), and an oxygen intake measurement module (64), for controlling so as to transmit the physical strength and health information sensed in the sensor section to the main controller section (20).

9. A system according to claim 8, wherein said exercise equipment (10) comprises a brake handle (11) with the electrocardiogram measurement means (51), body fat measurement means (52), and grasping power measurement means (53).

* * * * *